US006817998B2

(12) United States Patent
LaHaye

(10) Patent No.: US 6,817,998 B2
(45) Date of Patent: *Nov. 16, 2004

(54) METHOD AND APPARATUS FOR MONITORING LASER SURGERY

(76) Inventor: Leon C. LaHaye, 566 Sand Pit Rd., Arnaudville, LA (US) 70512

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/816,175

(22) Filed: Mar. 26, 2001

(65) Prior Publication Data

US 2001/0056276 A1 Dec. 27, 2001

Related U.S. Application Data

(63) Continuation-in-part of application No. 09/359,371, filed on Jul. 23, 1999, now Pat. No. 6,322,555.

(51) Int. Cl.[7] ............................................. A61F 9/007
(52) U.S. Cl. ............................ 606/11; 606/5; 606/10; 606/13; 606/17
(58) Field of Search ............................ 606/3, 5, 10–13

(56) References Cited

U.S. PATENT DOCUMENTS

| 4,061,925 A | 12/1977 | van der Gaag et al. |
| 4,464,960 A | 8/1984 | Roepers et al. |
| 4,669,466 A | * 6/1987 | L'Esperance ............... 606/5 |
| 4,695,697 A | 9/1987 | Kosa |
| 4,729,372 A | 3/1988 | L'Esperance, Jr. |
| 4,784,135 A | 11/1988 | Blum et al. |
| 4,792,690 A | 12/1988 | McCann et al. |
| 4,911,711 A | * 3/1990 | Telfair et al. ............... 606/5 |
| 4,916,319 A | * 4/1990 | Telfair et al. ............... 250/365 |
| 4,941,093 A | 7/1990 | Marshall et al. |
| 4,973,330 A | 11/1990 | Azema et al. |
| 4,994,059 A | 2/1991 | Kosa et al. |
| 5,002,051 A | 3/1991 | Dew et al. |
| 5,012,202 A | 4/1991 | Taylor |
| 5,108,388 A | 4/1992 | Trokel |
| 5,123,902 A | 6/1992 | Muller et al. |
| 5,154,707 A | 10/1992 | Rink et al. |
| 5,196,006 A | 3/1993 | Klopotek et al. |
| 5,219,343 A | 6/1993 | L'Esperance, Jr. |

(List continued on next page.)

OTHER PUBLICATIONS

PCT Written Opinion relating to PCT Application PCT/US02/07184, dated Jun. 19, 2003; from the International Preliminary Examining Authority.

SVS Apex, 6.5mm Holmium/Excimer Laser System User's Manual, Operation and Maintenance, Rev. B, pp. 2–15, 26, 27, 3–11, 6–11 through 6–13, 6–14 through 6–17, 6–25 through 6–38, 8–4 through 8–8, 8–19 through 8–25, 9–1, 2, 8, 10, 11, and 13. (Summit Technology, Inc.) (1/95).

PM1 Calibration Procedure Service Manual, pp. 5.3–1 through 5.3–5, 5.4–1 through 5.4–6, and Star Printout Customer Information (Summit Technology, Inc.) (1/95).

Primary Examiner—David M. Shay
(74) Attorney, Agent, or Firm—Burns, Doane, Swecker & Mathis, L.L.P.

(57) ABSTRACT

A method and system for laser surgery produces controlled laser pulses and simultaneously verifies that a correct sequence of pulses are being delivered to the patient. A photo detector receives a predetermined portion of the energy of the treatment pulses as they exit the system. A separate monitoring computer compares an output signal from the photo detector with reference information for the treatment sequence. The system is exemplified in an implementation in an ophthalmic laser surgery system.

36 Claims, 8 Drawing Sheets

U.S. PATENT DOCUMENTS

| | | |
|---|---|---|
| 5,219,344 A | 6/1993 | Yoder, Jr. |
| 5,225,884 A | 7/1993 | Stark et al. |
| 5,284,477 A * | 2/1994 | Hanna et al. ............. 606/5 |
| 5,324,281 A | 6/1994 | Muller |
| 5,423,801 A | 6/1995 | Marshall et al. |
| 5,752,950 A | 5/1998 | Frey et al. |
| 5,772,656 A | 6/1998 | Klopotek |
| 5,891,131 A | 4/1999 | Rajan et al. |
| 5,984,916 A | 11/1999 | Lai |
| 6,074,382 A | 6/2000 | Asah et al. |
| 6,080,148 A | 6/2000 | Damasco et al. |
| 6,090,100 A * | 7/2000 | Hohla .................. 606/5 |
| 6,099,522 A | 8/2000 | Knopp et al. |
| 6,322,555 B1 * | 11/2001 | LaHaye ................ 606/10 |

* cited by examiner

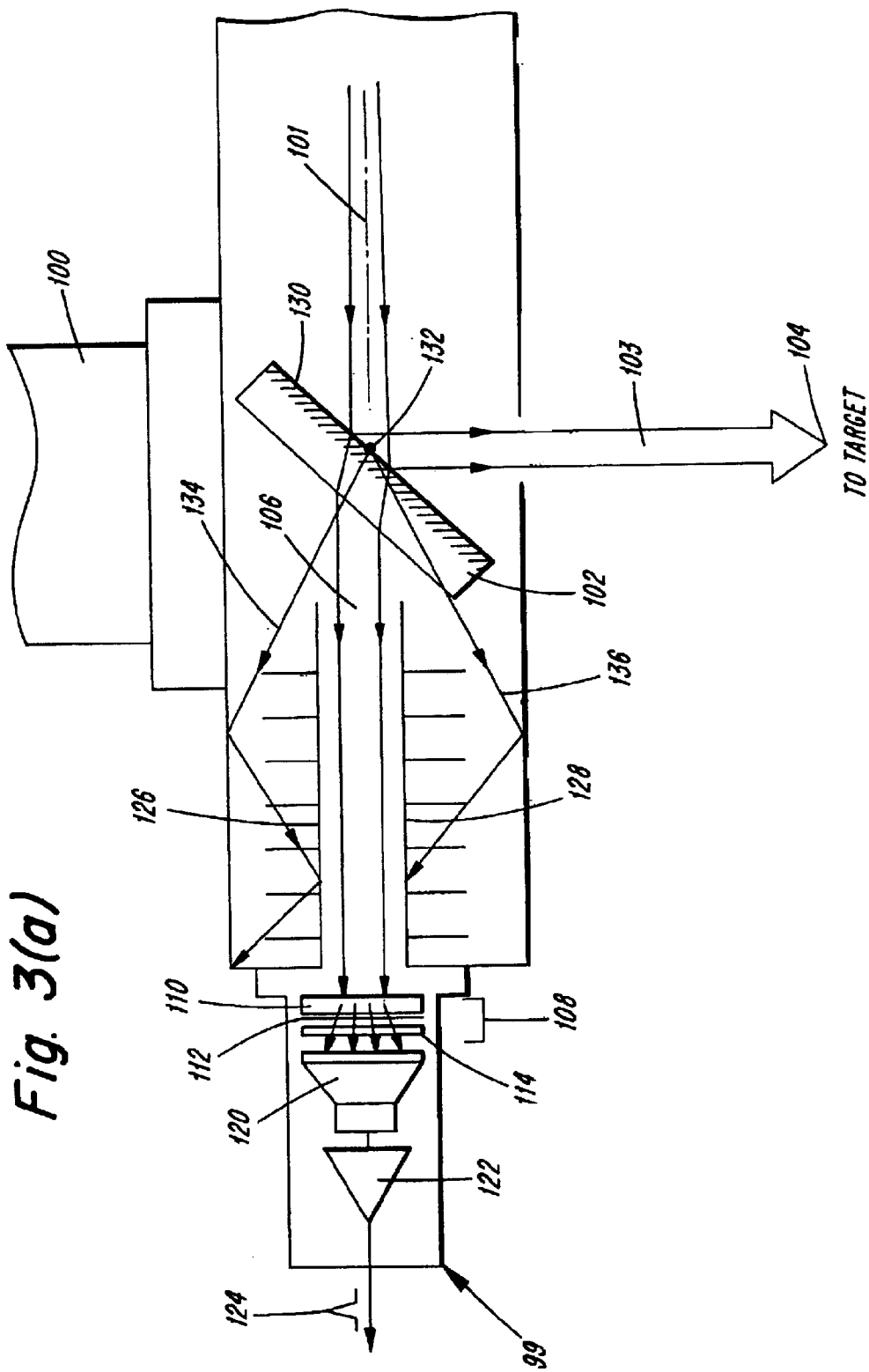

METHOD AND APPARATUS FOR MONITORING LASER SURGERY

RELATED APPLICATIONS

This application is a continuation-in-part of U.S. application Ser. No. 09/359,371, filed Jul. 23, 1999, now U.S. Pat. No. 6,322,555 the contents of which is hereby incorporated by reference.

FIELD OF THE INVENTION

This invention relates to laser surgery apparatus and methods adapted for use, for example, in the monitoring of laser systems used in ophthalmic laser surgery.

BACKGROUND OF THE INVENTION

Laser systems have been used in ophthalmic surgery for modifying the cornea of the patient. Systems such as shown in U.S. Pat. No. 4,729,372 to L'Esperance contemplate the controlled ablation of the cornea of the patient with a pulsed excimer laser. Operations performed with the system include corneal transplants and keratotomics.

The application of laser light to the cornea may be controlled by spot scanning of the cornea or by the use of masks. As shown in U.S. Pat. No. 5,108,388 to Trokel, the masks may, for example, employ slits or holes. Repeated scanning or pulsing through properly selected masks are employed to reshape or reprofile the curvature of the cornea to treat myopic or hyperopic conditions. The system can also be used, for example, to remove corneal sections for corneal replacements or transplants.

Three types of laser vision correction surgery techniques are known in the art: broad beam, slit scanning and spot scanning. Broad beam systems use a relatively large beam (e.g. 6.0 to 8.0 mm) pulsed at a relatively low pulse rate (e.g. 10 to 50 Hz). The spot delivered to the cornea may be, for example, from ½ mm to 8 mm in diameter depending on the iris opening of the system set to various positions in accordance with a treatment sequence for the patient. Spot scanning systems also called "flying spot" scanners typically employ reciprocating or rotating optical devices to make a series of overlapping laser shots, that for example, spiral out from the center of the cornea. Spot scanning systems use a relatively small spot (e.g. 1 to 2 mm in diameter). A typical treatment using a spot scanning system may require several thousand shots at 50 to 200 Hz. In a slit scanning laser, the laser beam is focused through a slit in a rotational device. The slit may be gradually enlarged to increase the ablated area on the cornea. Various scanning systems are described, for example, in U.S. Pat. No. 6,136,012 to Chayet et al., which is hereby incorporated by reference.

A system used by applicant for performing ophthalmic laser surgery is shown in FIG. 1. The system includes an Excimer laser 10 such as a COMPex 201 Excimer laser. An optical rail 12 contains optical elements for controlling the laser pulses and delivers spatially modulated pulses to a shuttling device 14, which acts as a selectively positionable turning mirror, for directing the laser pulses to a selected one of the two surgical stations, 16 and 18. The system allows surgery to be performed on one patient while a second patient is readied, and improves the utilization efficiency of the operating room, laser and optical rail.

FIGS. 2(a) and (b) are vertical and horizontal cross-sectional views and ray traces of an optical path which may be used in the system of FIG. 1 to deliver pulses from the laser 10' to the cornea of the patient at 20. A light beam from the laser is shaped and focused by a series of lenses 22, 24 and 26. A beam homogenizer 28 is located next in the optical path as shown. A spatial modulator 30 provides beam dimensions and orientations in accordance with predetermined treatment parameters appropriate for the surgery required by the patient. The spatial modulator may include a conventional iris and variable, slit mask(s) as well as controls for changing the axis of orientation of the mask(s). These systems are motor driven on command from a treatment computer containing a treatment algorithm into which the treatment parameters have been programmed.

The shuttling turning mirror 32 selectively directs the laser beam to one or the other surgical stations along one of the system arms 34 or 36 shown in FIG. 1. An imaging lens 38 is located in each arm. Pulses from the imaging lens are reflected by end turning mirror 40 toward the target area 42 on the patient's cornea.

It is important that pulses delivered to the cornea have the appropriate energy to ensure that the reprofiling, cutting or ablation produced is consistent with the prescribed treatment for the patient. Systems of the type shown in FIG. 2 have employed photo detectors selectively positionable in the main optical path of the system at the end turning mirror for the purpose of calibrating or adjusting the energy delivered by the system during a preliminary calibration phase. See U.S. Pat. No. 5,772,656 to Kloptek.

Other control systems have been proposed such as disclosed in U.S. Pat. No. 4,941,093 to Marshall et al., which includes a measurement device to measure the cornea surface profile and a feedback control system to control the laser operation in accordance with the measured and desired profiles. U.S. Pat. No. 5,423,801 to Marshall et al. discloses further control of the laser by a measurement signal from a beam-shaping means and/or cornea while it is exposed to irradiation by the laser. U.S. Pat. No. 4,973,330 to Azema et al. discloses a photo detector associated with a semi-transparent mirror, which is intended to furnish a treatment computer with information relative to the energy of the pulses exiting the laser before the laser beam reaches the controlling device. A laser calibration device is shown in U.S. Pat. No. 5,464,960 to Hall et al. which employs a phantom cornea with superimposed thin films of alternating colors. U.S. Pat. No. 5,984,916 to Lai discloses a surgical laser system with a feedback system for controlling the treatment laser beam.

OBJECTS AND SUMMARY OF THE INVENTION

It is an object of the present invention to provide a more efficient and reliable technique for monitoring laser surgery, including broad beam, slit scanning and spot scanning systems.

It is another object of the present invention to monitor the energy of actual laser pulses used in the ophthalmic laser surgery as they exit the optical rail.

It is another object of the present invention to monitor a sequence of laser pulses of varying beam dimensions and locations used in ophthalmic laser surgery.

It is another object of the present invention to provide a parallel, fail-safe system for detecting discrepancies between a programmed treatment and the laser pulses actually administered to the cornea of the patient.

These and other objects and features will be apparent from the following description of the present invention contained herein.

The present invention relates to methods for laser surgery and particularly for the modification of the cornea of a patient with a laser system in accordance with treatment parameters appropriate for the patient and for continuously verifying that a predetermined sequence of laser pulses of correct energy are being delivered to the cornea of the patient. In practicing the method, pulses of laser light are generated and controlled. The controlled pulses are simultaneously directed to the cornea of the patient and to a photo detector. Advantageously, the system uses a beam splitter for this purpose. The beam splitter is the last optical element in the optical path leading to the cornea of the patient. An output signal of the photo detector is converted into a value representative of the light energy delivered to the cornea of the patient. Alternatively, the photo detector may be a two-dimensional array of photo sensing cells capable of producing signals indicative of the spacial energy distribution of the treatment pulses. Such an array may, for example, be a CCD or CMOS device.

Light energy values may be compared to a reference values derived from system calibration information and from the treatment parameters for the patient. An indication of the performance of the laser system is provided in response to this comparison. When a two-dimensional detector array is used, a histogram may be produced, displayed and stored showing the amount of energy delivered to incremental areas of the cornea over selected time intervals.

In preferred embodiments of the invention, the pulses of laser light are produced by a laser triggered by a triggering signal from a treatment computer. The pulses of laser light may be spatially modulated or scanned responsive to signals from the treatment computer. The treatment computer is programmed with the treatment parameters appropriate for the patient. In this embodiment, the reference values are produced by a monitoring computer separately programmed with the treatment parameters appropriate for the patient. The double entry of treatment parameters helps expose data entry errors in the treatment computer, since such an error will create a discrepancy between the light energy value and the reference value. The comparison may be initiated by the monitoring computer responsive to the laser triggering signal. When the light energy value of a predetermined number of pulses deviates a predetermined amount from the corresponding reference values, the system may produce an alarm signal or shut down the system.

In another preferred embodiment of the present invention, the simultaneous directing of the spatially modulated pulses is performed by beam-splitting the pulses to direct a portion of electromagnetic energy from the pulse to a photo detector. The directed portion of electromagnetic energy of the laser pulse may be directed through an optical baffle to block scatter caused, for example, by fluids splashed on the beam splitter. The directed portion of the pulse may then be converted to fluorescent light which is detected by the photo detector. One or more neutral density filters may be employed to filter the fluorescent light so that the photo detector and associated amplifier are operated in a generally linear response mode across a range of expected incident radiation energies.

The present invention also includes an apparatus for producing a predetermined treatment sequence of laser pulses of predetermined energy and and for monitoring the energy of the pulses as the pulses are being delivered to the patient. Such an apparatus may include an excimer, pulsed laser, and a beam homogenizer and a spatial modulator in the optical path of the laser. First electronic circuitry controls the laser and spatial modulator in accordance with entered data indicative of the predetermined treatment sequence of pulses for the patient. Second electronic circuitry produces reference values indicative of the energy of laser pulses which should be produced by the laser, the reference value being calculated in accordance with separately entered data indicative of the predetermined treatment sequence of pulses for the patient. Advantageously, the first and second electronic circuitry are separate, programmable digital computing devices.

A photo detector produces a monitoring signal related in value to the energy of laser pulses delivered to the patient. Further electronic circuitry compares the monitoring signal with the corresponding reference value calculated by the second electronic means.

As noted above, the delivered laser pulses may be monitored using a beam splitter which is the last optical device in the system optical path leading from the laser to the cornea of the patient. Advantageously, a second beam splitter and a photo detector may be placed at the beginning of the optical rail to monitor laser output directly. This monitoring may be required because the output of the laser may vary from pulse to pulse or drift over the course of a single patient treatment. Advantageously, this additional detector is capable of detecting an energy change of 2% or less from pulse to pulse. Detected changes greater than a selected threshold level may be used to produce a warning signal or to shut down the system.

The foregoing is intended as a convenient summary of this disclosure. However, the scope of the invention intended to be covered is indicated by the patent claims.

BRIEF DESCRIPTION OF THE DRAWINGS

FIG. 3(a) is a horizontal cross-sectional view of a laser energy monitor with an optical baffle in accordance with a preferred embodiment of the present invention;

DETAILED DESCRIPTION OF PREFERRED EMBODIMENTS

The fail-safe systems disclosed are based on the control and monitoring of the energy in the laser beam exiting the optical rail and beam controlling optics of a laser surgery system. In preferred embodiments, the fail-safe system includes a laser energy monitor, analog-to-digital converter, and a programmed monitoring computer.

Figure 1:
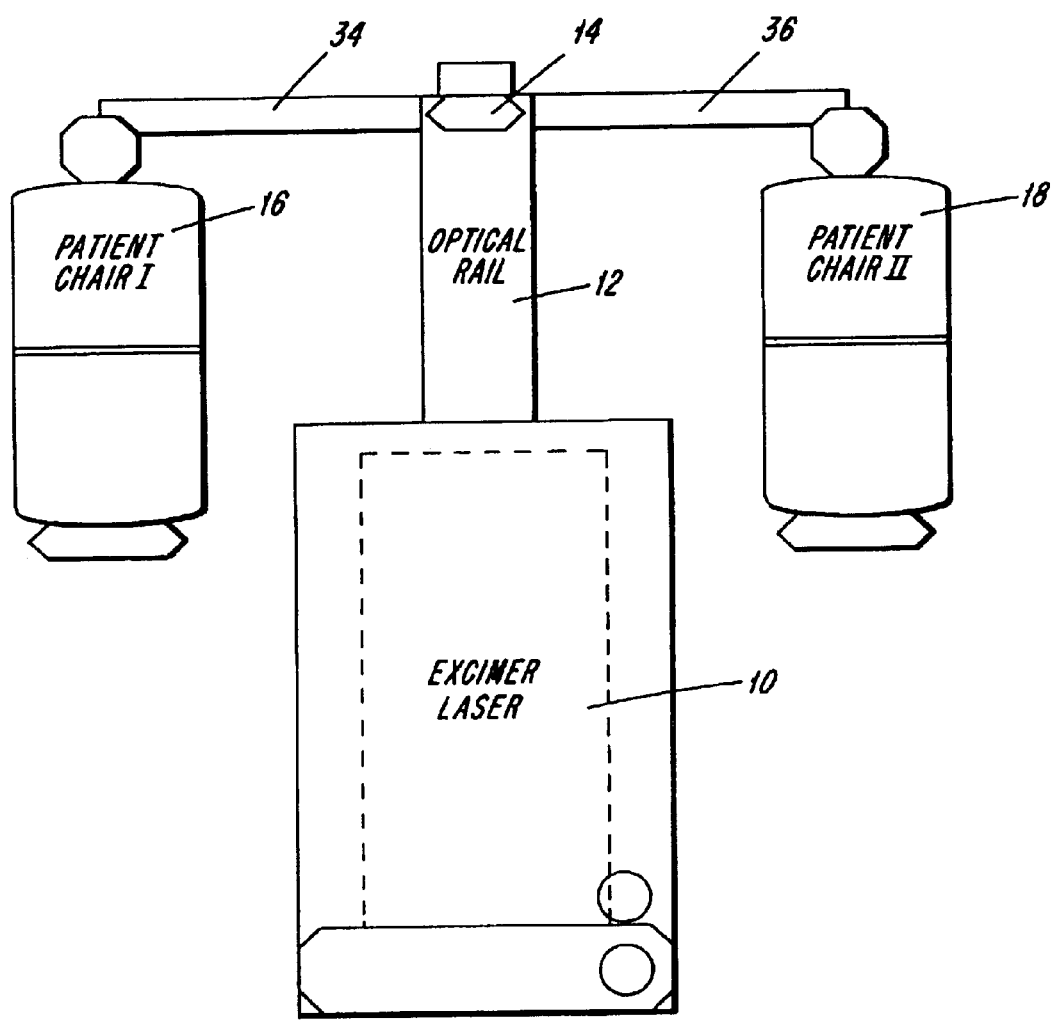
FIG. 1 is a plan view of a two surgical station laser eye surgery system.
Figure 2A:
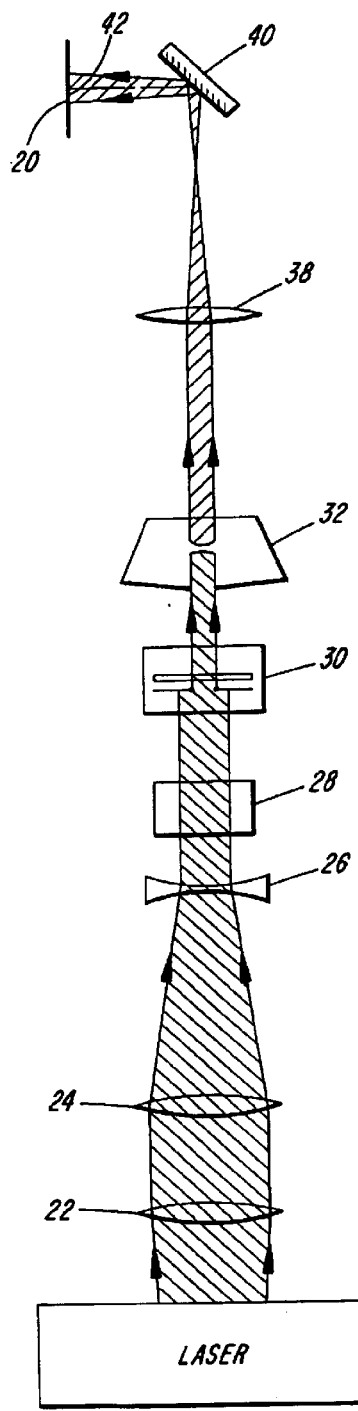
FIGS. 2(a) and (b) are, respectively, vertical and horizontal cross-sectional views of the optical path employed in the system of FIG. 1 for delivering laser pulses to the cornea of the patient.
Figure 2B:
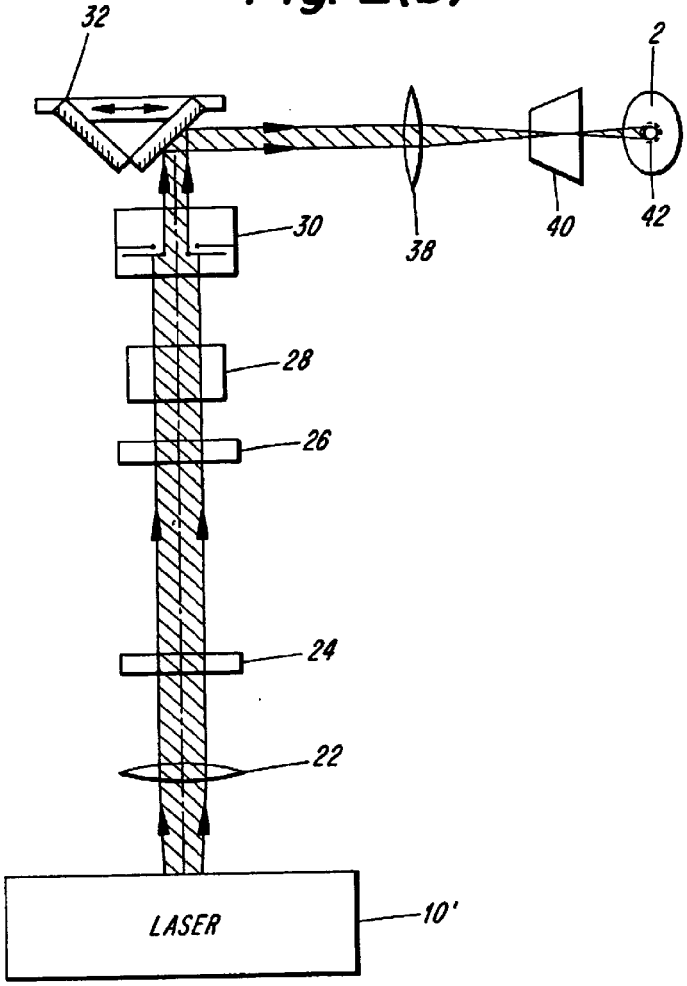

The monitoring system may be used, for example, in the two patient ophthalmic surgical arrangement shown in FIG. 1. In such a case, two identical laser energy monitors may be installed at the ends of the right and the left laser beam delivery systems (surgical stations) after the end 45° turning mirror. As discussed in greater detail below, each energy monitor may consist of a glass fluorescence filter, converting laser radiation into fluorescence light, and a silicon photo diode for light detection. To operate the diode and the signal amplifier in linear modes, several neutral density filters are used. The amplified photo diode signal goes to the analog-to-digital converter (preferably a circuit card installed into the monitoring computer or an additional computer).

Two independent computers may be used in the most preferred embodiment of the present invention. One computer is the treatment computer, the second computer is the monitoring or fail-safe computer. The treatment computer drives the iris/slit/axis motors in the spatial modulator and generates the appropriate trigger pulses to the laser according to a treatment/calibration algorithm.

The monitoring computer measures, records, and monitors the energy detected by the energy detector for each pulse fired. The monitoring computer compares the energy values of the treatment algorithm to a predetermined calibration curve and simultaneously runs fail-safe algorithms. The treatment algorithm and the monitoring algorithm are equivalent. The monitoring computer receives the triggering signal sent to the laser by the treatment laser. Live and simultaneous monitoring of the entire treatment dose is performed by the system.

To avoid rather complicated calculations of iris, mask or spot geometrical area and the influence of functional non-linearity of the photo diodes and A/D converter or measurement accuracy, a calibration curve approach may be used. A calibration curve is generated at the beginning of every surgery period. This is accomplished with an initial calibration process. The calibration curve may be generated by running a calibration algorithm on the treatment laser and measuring and storing measured pulse energy values for each slit and iris setting from 6.0 mm down to 1.0 mm with 0.5 mm increments. The fail-safe computer program generates a calibration curve based on the photo diode signal value of an average of 20 consecutive laser pulses taken at each position of the iris and slit. When a treatment ablation algorithm is executed, the monitoring computer receives, after every laser pulse the digitized photo detector signal which is compared to a reference value obtained from the calibration curve, the reference value indicating the expected energy value for the particular spatial dimensions of the pulse then being administered.

The monitoring computer software compares the measured energy value with a reference value determined from the treatment parameters and treatment algorithm. Even though the system monitors laser pulse energy, its comparison with reference values from the calibration curve for the proper iris/slit dimension is equivalent to monitoring the energy of the ablating laser beam.

The monitoring computer may be programmed with values of acceptable deviation between the monitored energy and reference energy values. For example, an acceptable deviation in treatment energy may include +/−10% deviation range from the calibration curve. If 10 consecutive laser pulses are outside of the above assigned ranges, the monitoring computer initiates a continuous warning beep, and after 3 seconds will interrupt the laser triggering through a relay block unless the laser operator does so earlier.

Both the treatment and monitoring computers track and store all data of a patient's treatment algorithm, energy etc. and if the treatment is interrupted or stopped, the treatment data will be available to resume treatment after the problem is resolved. Fail-safe features incorporated into the system include a maximal/minimal range of treatment energy, storage of treatment data, and an uninterruptable power supply system to maintain both the treatment computer and the monitoring computer in the event of a power failure.

Monitoring proper operation of the iris/slit mechanism is a function of the monitoring computer software, and is accomplished through comparisons of measured energy values by the photo diode with expected energy values for the specific treatment algorithm and the particular iris/slit dimensions called for by the algorithm. For example, the treatment computer could signal the iris to be 4 mm. However, the iris may be "stuck" at 5 mm. The fail-safe system would monitor the pulse and indicate too high an energy value as compared with the reference value for the expected 4 mm iris. A value associated with the "stuck" 5 mm iris would be recorded.

Another feature of the laser dual computer fail-safe system requires the operator to enter the patient treatment data twice, once into the treatment computer and a second time into the monitoring or fail-safe computer. This dual entry requirement provides for an opportunity to double-check the current patient name, eye, and desired correction for refractive error.

Details of the system of the present invention will now be described with reference to the drawings.

Figure 3:
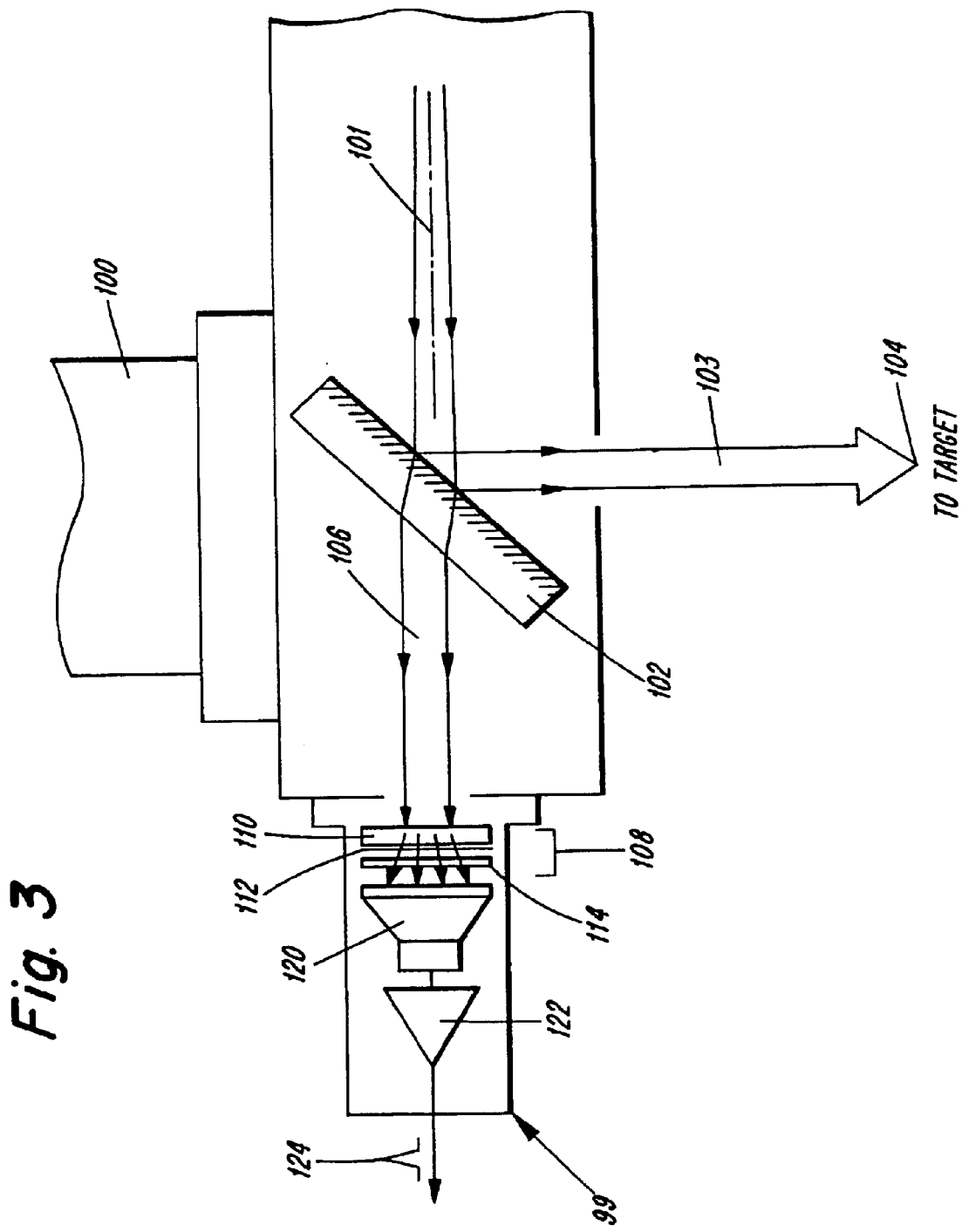
FIG. 3 is a horizontal cross-sectional view of a laser energy monitor in accordance with a preferred embodiment of the present invention.

FIG. 3 is a cross-sectional side elevation of a portion of an arm of the system of FIG. 1 including a laser energy monitor 99 and a surgical microscope mount 100. A laser beam from the optical rail and shuttling device is shown at 101. The pulses making up the beam have already been spatially modulated. The beam impinges on a beam-splitter 102. In preferred embodiments, the beam splitter is a fused silica coated glass plate with a principle plane oriented at a 45° angle with respect to the laser beam 101. The front surface of the plate 102 may reflect approximately 95% of the energy of the laser beam (reflected beam 103) to the target as indicated at 104. A low energy transmitted beam 106 passes through the beam-splitter and impinges on a detector optical system 108. In preferred embodiments the detector optical system includes a glass filter/diffuser 110 which diffuses the laser light. Advantageously, a fluorescent media 112 is located at the diffuser. The fluorescent media may have the effect of changing the wavelength of the incident light. For example, diffused 193 nm laser radiation may be converted into blue-green fluorescent light.

One or more neutral density filters 114 may be provided to reduce the intensity of the light received by the photo detector, such as photo diode 120. This intensity reduction is provided to permit the photo detector and associated analog amplifier 122 to operate in a generally linear response mode across a range of expected incident light energies.

The amplifier 122 produces a signal 124. In preferred embodiments, the signal is a voltage pulse which is selected by time-windowing circuitry in the monitoring computer. The windowing is triggered by the triggering of the laser system to produce a treatment pulse. The peak height of the voltage pulse is used as an indication of the energy of the treatment pulse delivered to the patient, as will be discussed below.

FIG. 3(a) illustrates an alternative embodiment of FIG. 3 in which similar features are identified by like numerals. In FIG. 3(a) optical baffles 126 and 128 have been located between the photo detector 120 and the beam splitter 102. The optical baffles are arranged to absorb scattered light, including light not properly reflected from the front surface 130 of the beam splitter 102. Such scattered light may, for example, be produced by organic or lens deposits or debris such as fluids spattered on the beam splitter during surgery. Such a deposit is depicted at 132. Beams 134 and 136 represent light scattered by the deposit at 132 and absorbed within the optical baffles 126 and 128. The baffle improves sensitivity of the measurement, for example, by excluding light energy from measurement which has been scattered and thus is not indicative of energy delivered to the cornea of the patient. Fluorescence of organic materials may be also reduced or eliminated by gating the photo-detector.

Figure 4:
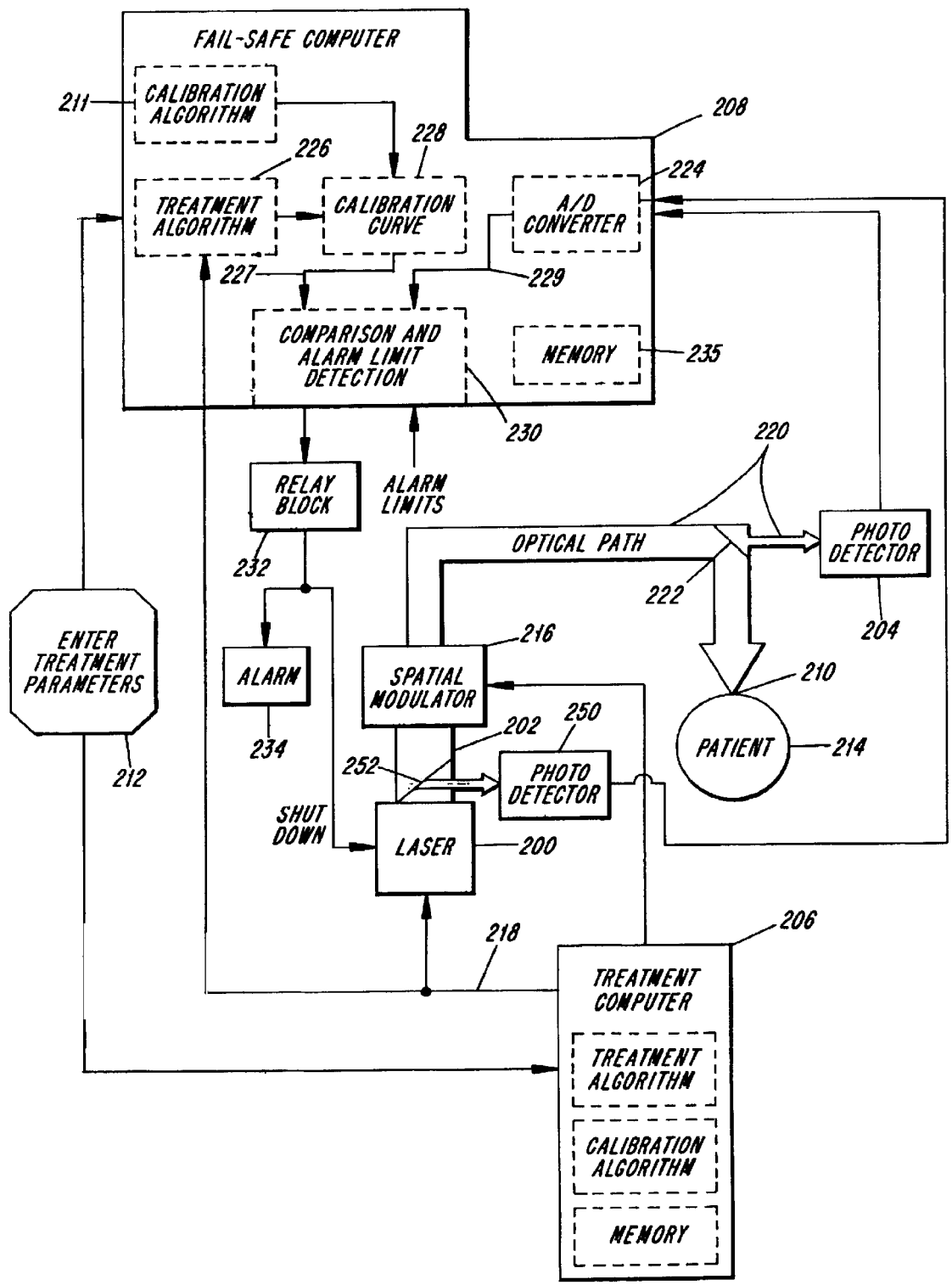
FIG. 4 is a schematic block diagram illustrating process and apparatus aspects of the disclosed system for producing and monitoring laser pulses delivered to the cornea of a patient in accordance with the present invention.

FIG. 4 is a schematic block diagram illustrating aspects of the method and system of the present invention. The system includes a laser 200, optical rail 202, photo detector 204, treatment computer 206 and fail-safe computer 208.

In operation, the system is initially calibrated by placing a laser light energy detector at the location 210 and producing a series of test pulses having various spatial modulation under the control of the calibration algorithm of the treatment computer. At the same time energy is monitored using photo detector 204 such as an energy monitor and fail-safe computer 208. The fail-safe computer develops a calibration curve or data using the calibration algorithm 211 and monitored energy values.

More specifically, in the calibration mode, an average of measured energy values from the A/D converter are associated with the various spatial modulator settings. The result is a calibration curve or look-up table which correlates various spatial modulator settings with an average voltage measurement from the energy monitor during the calibration mode.

Treatment parameters are entered for a particular patient as indicated at 212. The treatment parameter may include sphere correction, cyl correction and cyl axis values. The data entry is made separately to both the treatment computer 206 and the fail-safe computer 208. The patient 214 is readied for surgery.

The treatment computer 206 generates a treatment sequence of pulses and controls the spatial modulator 216 in accordance with commands derived by a conventional treatment algorithm from the treatment parameters. The laser 200 is triggered by signals on control line 218. These trigger signals are simultaneously provided to the fail-safe computer 208.

Pulses produced by the laser 200 are spatially modulated and travel along optical path 220. The beam splitter 222 reflects the pulses to the patient's cornea and transmits a portion of the beam to the photo detector 204. Signals from the photo detector are applied to the A/D converter 224, which may be part of the circuitry hardware of the fail-safe computer 208.

Pulses from control line 218 and data entered as treatment parameters are processed by the treatment algorithm 226 resident in the fail-safe computer 208. The monitoring computer calls up a valve from the calibration curve or look-up table which corresponds to the spatial modulation of the pulse being administered. The result is a reference value related to the prescribed energy for the being pulse delivered to the patient. This reference value is indicated at 227. The reference value is compared to a monitor energy value 229 derived from the signal from the photo detector 204. The comparison is indicated at 230.

Alarm limits may be input to the fail-safe computer 208. The alarm limits are employed to generate a control or alarm signal which is output to the relay block 232. The relay block may trigger alarm 234 or command a shut down of the laser 200.

Calibration data, treatment parameters, energy monitor data, alarm limits and comparison data may be stored in a memory 235 in fail-safe computer 208.

The system described above has been tested in an ophthalmic surgery excimer laser system. The laser output at each surgical station was set at 38 mJ at 6 mm of iris opening by adjusting the high voltage setting of the excimer laser. The corresponding digital value of photo diode signal was set as a reference energy value. Initial qualitative tests at 6 mm iris/slit opening included blocking of about 12% of laser aperture at different points. In all cases, the fail-safe mechanism worked properly reacting to the energy deficiency in the beam. Quantitative tests consisted of intentional decrease/increase of laser energy output by adjusting the excimer laser voltage at different iris/slit positions. A JMAX 43/EM400 energy meter was used to measure the output laser energy at the treatment plane. The following table presents the test results:

| Iris/slit opening (mm) | | Initial energy, | Shut Down Energy | | | |
|---|---|---|---|---|---|---|
| Iris | Slit | mJ | mJ | + % | MJ | - % |
| 1.5 | open | 2.6 | 2.9 | 11 | 2.3 | 11 |
| 6.0 | 2.0 | 14 | 15.5 | 11 | 12.5 | 11 |
| 3.0 | open | 10.0 | 11.0 | 10 | 9.0 | 10 |
| 6.0 | 4.5 | 25 | 27.5 | 10 | 22.5 | 10 |
| 5.0 | open | 27 | 30.0 | 11 | 24.4 | 10 |

Additional tests were conducted to simulate a variety of malfunctions of the iris/slit mechanism. This was accomplished by entering values in the treatment algorithms that simulated both partial and complete "sticking " of both the iris and slit while operating the monitoring fail-safe computer with the correct algorithms.

In all cases, the fail-safe system detected the errors by sounding an alarm and recording energy values that were either too high or too low with respect to the expected value for the proper iris or slit dimensions.

The test results show that the fail-safe mechanism operated in accordance with its design. The dual computer fail-safe method monitors the operation of the iris/slit mechanism, the quality of the optics, firing mechanism and ablation algorithm as well as the laser itself during the actual patient treatment. The results show that the fail-safe mechanism operated in accordance with its design. Its implementation is expected to provide higher safety level for patient laser refractive treatments.

Optionally a second photo detector 250 may be employed to directly monitor the output of the laser 200 at the beginning of the optical rail. Advantageously, a beam splitter 252 directs a portion of the laser pulses produced by the laser 200 to the photo detector 250. Output signals from the photo detector are monitored by the fail safe computer 208. The purpose of this additional detector is to provide normalization of laser output fluctuations, thereby increasing the sensitivity of the fail safe system. This is important because lasers in conventional commercial systems fluctuate 10% or more from pulse to pulse and may exhibit as much as a 50% drop in output over a single patient treatment. By incorporating this additional detector, the fail safe system should be able to detect 2% or less in energy changes from pulse to pulse. Signals obtained by the photo detectors 250 and 204 may be used by the fail safe computer to differentiate performance anomalies caused by the laser from those caused by components failures in the optical rail or foreign material on the optical surfaces of the system.

Figure 5:
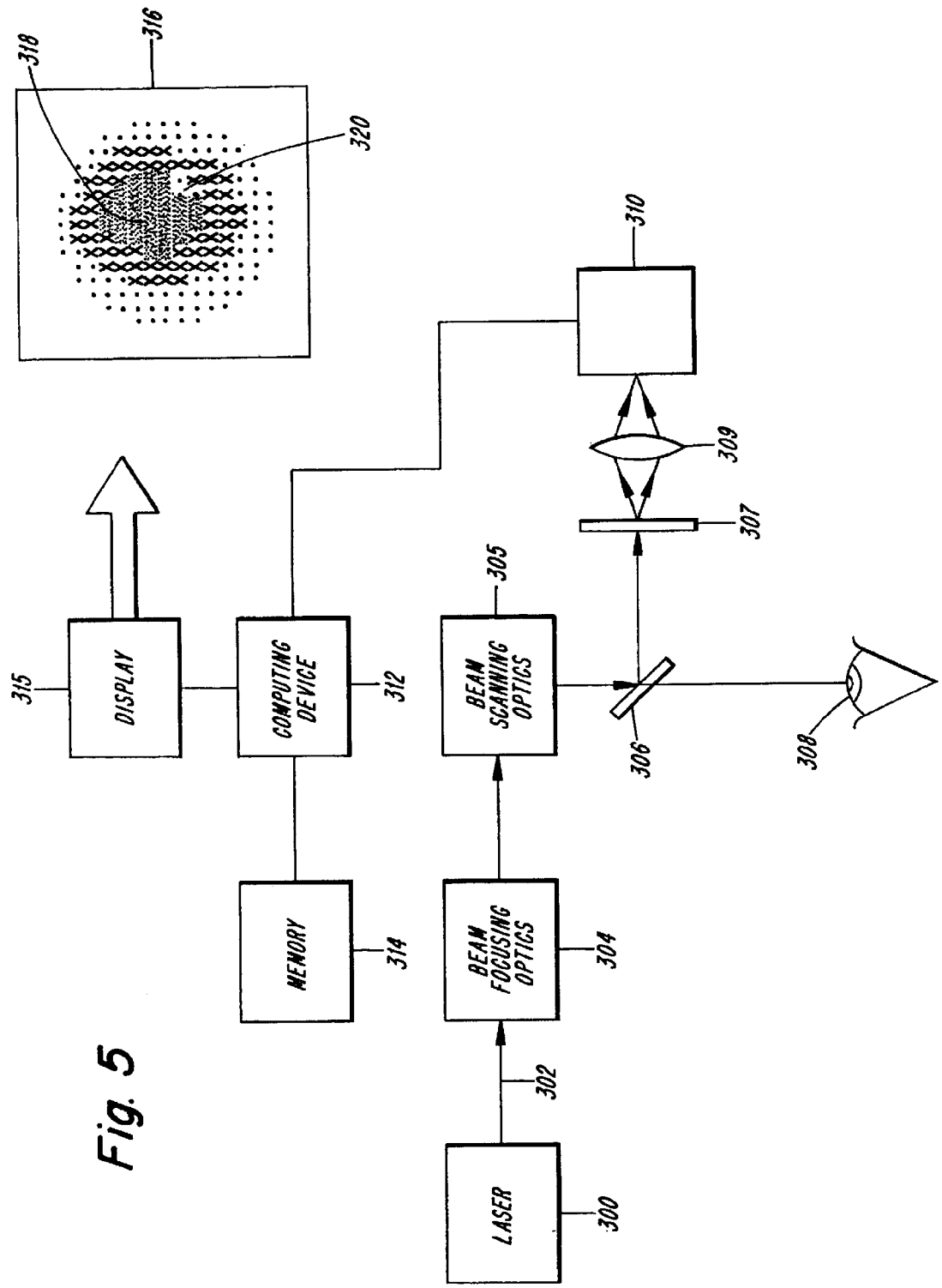
FIG. 5 is a schematic block diagram illustrating the use of an area array detector and histogram in a scanning spot laser surgery system in accordance with a preferred embodiment of the present invention.

FIG. 5 is a schematic block diagram illustrating the use of an area array photo detector and histogram in a scanning spot laser surgery system in accordance with a preferred embodiment of the present invention. In FIG. 5, a laser 300 produces a beam 302 which is focused to a relatively small spot size by beam focusing optics 304. The focused beam is scanned by beam scanning optics 305 in accordance with a treatment program in the conventional manner. A beam splitter 306 transmits a portion of the scanned beam to the cornea 308 of the patient. Another portion of the beam is reflected through the beam splitter 306 to an electronic camera 310 such as one employing an area photo detector such as a CCD. Preferably, the second portion of the beam is directed to a luminescent screen 307 located at the same distance from the scanner as the plane of the patient's cornea. The screen 307 converts the laser beam to visible light. An imaging lens 309 focuses an image of the beam or spot pattern for use by the electronic camera 310. A computing device 312 receives signals from the electronic camera and produces signals representative in value of the spacial energy distribution of one or a series of laser pulses. This information may be stored in memory 314, for example, to enhance patient records and/or for later evaluation the performance of the system or system drift. The signals may also be displayed, for example, on a display monitor 315. The display may take the form of a histogram such as that shown at 316. In the figure the blackened squares, Xs and dots represent pulse frequency and/or integrated energy delivered to particularly area increments on the cornea of the patient over a selected time interval or over the full treatment period. Generally, the histogram of the example shows a spherical energy delivery profile with the highest energy delivered to the center 318 of the cornea. An anomaly, for example, caused by fluid spattered on the beam splitter is shown by the energy drop-off at 320. It will be understood that such a histogram provides an effective indication of system malfunction.

Figure 6:
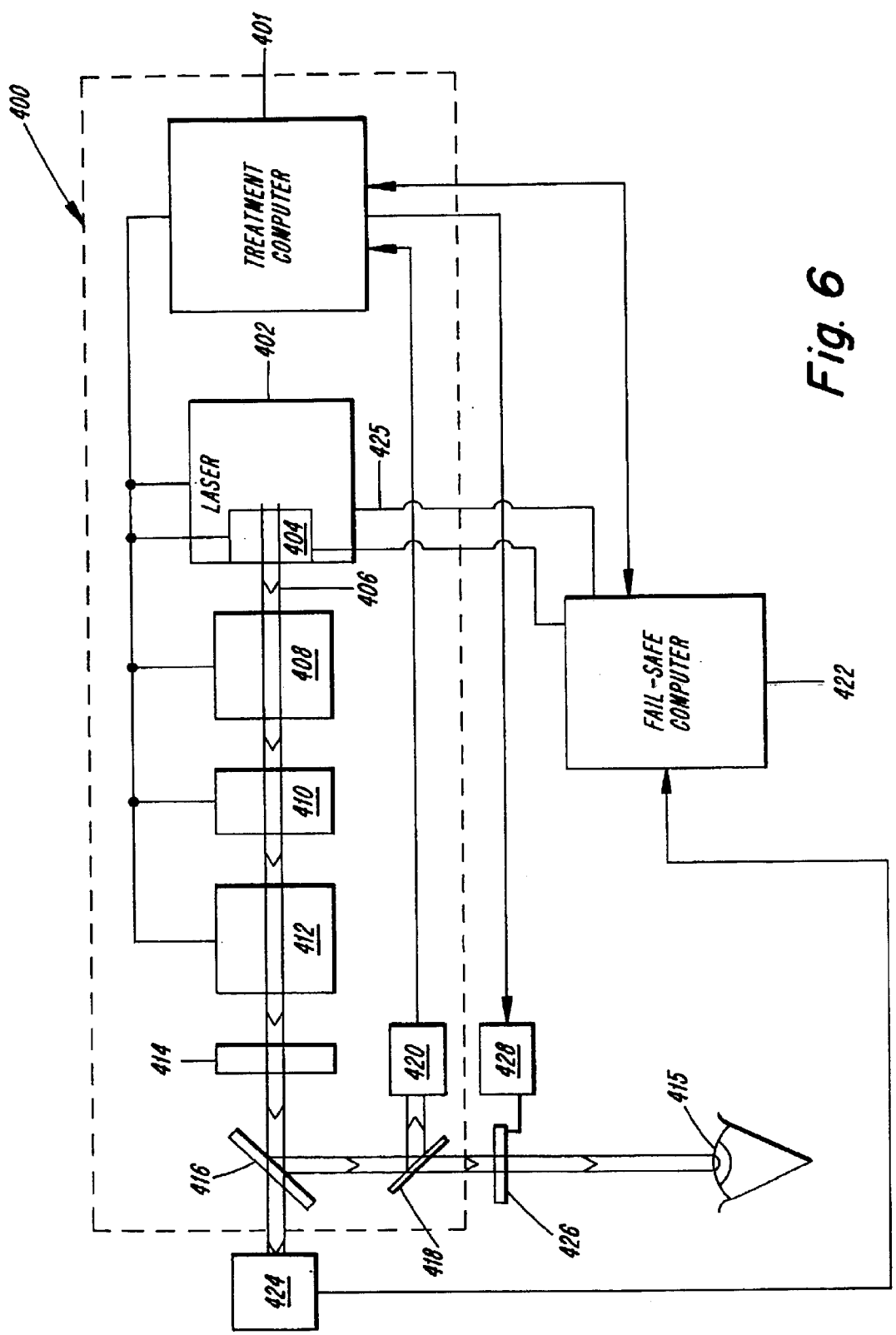
FIG. 6 is a schematic block diagram of a conventional broad beam laser surgery system retrofitted in accordance with the teachings of the present invention.

FIG. 6 is a schematic block diagram illustrating the retrofitting of a conventional broad beam laser surgery system in accordance with the teachings of the present invention. The apparatus within the dotted line box 400 represents a conventional broad beam laser surgery system such as an "SVS Apex" system manufactured by Summit Technology, Inc. The system includes a treatment computer 401 which controls a treatment sequence of pulses delivered to the cornea of the patient and a high output energy, low to moderate repetition rate excimer laser 402. A typical output of the laser is 200 to 300 mJ at 193 nm with a repetition rate of 10 to 40 Hz. The laser may include an internal laser output energy detector 404 to monitor the output pulse energy. After exiting the laser, the beam travels along optical path 406 to beam focusing optics 408, beam homogenizer 410, and beam shaper (iris and slit) 412 which operate under the control of the treatment computer 401. Imaging optics 414 creates the image of the beam shaper diaphragm in the treatment plane after the beam is turned toward the patient's cornea 415 by the turning mirror 416. Some such systems have an output beam splitter 418 and an energy monitor 420 for calibration purposes.

As shown in FIG. 6, the conventional broad beam laser surgery system 400 can be modified to provide real-time monitoring of the output laser pulses taking into account the actual dimensions of the iris/slit during treatment. For example, should the beam shaper fail after calibration, the system of FIG. 6 as modified could detect such a failure and prevent an incorrect ablation pattern being administered to the patent.

The retrofitting shown in FIG. 6 involves the addition of a fail safe computer 422 having some or all of the features of the fail-safe computer discussed above. The turning mirror 416 may be used as a beam splitter to permit transmission of a portion of the energy of the pulses being reflected by the turning mirror toward the patient. A photo detector system 424, such as of the type described in connection with FIG. 3(a) may be used to produce monitoring signals indicative of the laser pulses delivered to the cornea of the patient. The monitoring signals are transmitted from the photo detector system 424 to the fail-safe computer 422. The fail-safe computer may also receive a monitoring signal from the laser output energy detector 404. Finally, the fail-safe computer may send signals to and receive signals from the treatment computer related, for example, to the triggering of the laser and the current settings of optical elements 408, 410 and 412.

In operation, the system is first calibrated as discussed above. The evaluation of the laser pulses after they have passed through the controllable optical elements and normalization of these measurements using the signals from the laser output detector 404 will allow a significant improvement in monitoring the performance of the system and detection of the source of system malfunction, e.g., optical element failure, instability due to laser output fluctuations, etc. The use of digital electronics makes it possible to measure the energy of laser pulse striking the cornea with an accuracy of better than 1%. This is enough to track the difference between actual and programmed expansion of iris/slit mechanism within a few laser pulses. Further treatment can be halted in a timely fashion to avoid incorrect patient cornea ablation. This monitoring is made possible by the precise measurement of the energy of pulses directed at the patient and comparison of it with expected energy. As discussed above, this energy value is derived from a calibration curve at the appropriate dimension of the iris/slit diaphragm taken from each laser pulse in the predetermined treatment sequence for ablating the cornea of the patient. Thus, malfunctioning of the system such as malfunction of the iris/slit expansion mechanism, changes of laser output energy, change or loss of nitrogen purge, or sudden deterioration of system optics can be tracked by the fail-safe system and used to trigger system shut-off. Preferably, the fail-safe computer may be connected to the laser as indicated by line 425 to transmit a shut-down command directly to the laser and by-pass the treatment computer which itself may be the cause of the detected system malfunction.

To avoid a contamination of the output optics by accidental fluid splashes during cornea flap preparation, a shield transparent to visible light such as glass or plastic plate 426 may be provided. The shield is selectively positioned "in" and "out" of the optical path by a special driver 428.

The plate 426 may be located in the optical path when no laser ablation is being performed. Advantageously, the plate is of good optical quality, for example to permit observation of the cornea through the plate. The plate is moved out of the optical path during ablation, preferably on command from the treatment computer 401. Advantageously, the plate is disposable and is replaced periodically with a new plate to avoid build-up of contamination.

Figure 7:
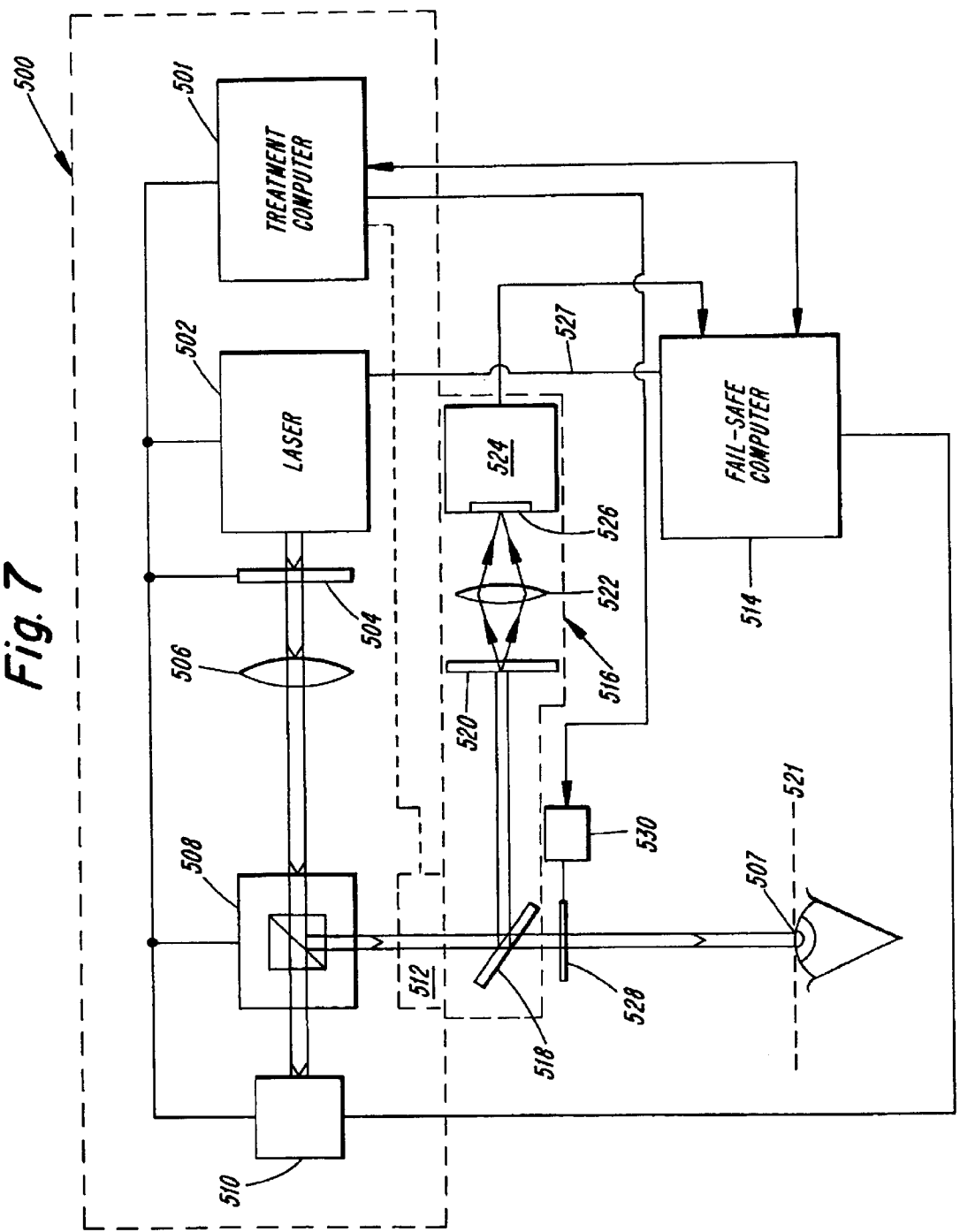
FIG. 7 is a schematic block diagram of a conventional scanning laser beam surgery system retrofitted in accordance with the teachings of the present invention.

FIG. 7 is a schematic block diagram illustrating the retrofitting of a conventional scanning beam laser surgery system in accordance with the teachings of the present invention. The apparatus within the dotted line rectangular box 500 represents a conventional scanning beam laser system such as a scanning beam laser surgery system using a 1 or 2 mm laser spot. The system includes a treatment computer 501 and a low pulse energy, high-repetition rate excimer laser 502. A typical output of the laser is 3 to 5 mJ at a repetition rate of 100 to 200 Hz. The optical rail of the system may include an iris diaphragm 504; a focusing lens 506 and an X-Y scanner 508 which acts as a turning mirror. The laser 502, diaphragm 504 and X-Y scanner 508 operate under the control of the treatment computer to provide laser pulses in accordance with a treatment sequence for the patient. The iris diaphragm 504 is set in the path of the beam, which is transformed by a focusing lens 506 into a sub-mm ablation spot to the cornea 507 of the patient after being reflected by two turning mirrors of the X-Y scanner 508. There is either an internal pulse energy monitor 510 or an external one installed right after the scanning mirrors. This monitor may be used in a feedback loop to maintain a stability of laser output, or just an energy monitor looped to the laser power supply to stop laser operation if the pulse energy goes outside of the preset limits. A conventional, optional eye tracker 512 under system control may also be provided.

As shown in FIG. 7 the conventional scanning beam laser surgery system 500 can be modified to provide real-time monitoring of the output energy distribution. The retrofitting involves the addition of a fail-safe computer 514 which functions to compare separately entered treatment program data with spatial energy distribution information obtained using an imaging system (dotted line box 516). The fail-safe computer operates in a manner similar to that described above.

In a preferred embodiment the imaging system 516 includes a beam splitter 518 on the optical path to the cornea of the patient. A portion of the beam energy (e.g. 5%) is reflected by the beam splitter 518 to semi-transparent, luminescent screen 520 located at the same distance from the scanner as the plane 521 of the patient's cornea. The screen converts 193 nm UV radiation into visible light. An imaging lens 522 focuses an image of the beam or spot pattern onto an electronic camera 524 which includes an area array photo detector such as a CCD chip 526.

The major purpose of the fail-safe system of FIG. 7 is to monitor the scanning pattern rather than just the total energy of pulses delivered to the patient.

Using the image obtained by the electronic camera 524 the fail-safe computer tracks the position of the scanning spot for each laser pulse and compares it with the ablation algorithm pattern of the predetermined treatment sequence. In case of an X-Y scanner malfunction, for example, there will be an obvious discrepancy between programmed and actual patterns. The fail-safe computer halts the operation of the system when a malfunction is detected, for example, by sending a shut-down command directly to the laser over control line 527.

While the CCD imaging system of FIG. 7 has been described in connection with the retrofitting of a scanning spot laser surgery system, it will be understood that such an imaging system may also be used in conjunction with a broad beam laser surgery system such as shown in FIG. 6.

To further improve the reliability of the entire system, a shield 528 and shield driver 530 may be provided similar in construction and function to the shield and driver discussed in connection with the system of FIG. 6. The shield and driver may operate under the control of the treatment computer 501.

While the present invention has been described with reference to certain preferred embodiments, the scope of the invention to be protected is determined by the following claims and their appropriate range of equivalents.

I claim:

1. A method for modifying the cornea of a patient with pulses of laser light in accordance with a treatment sequence comprising the steps of:
   generating pulses of laser light;
   controlling the pulses of laser light so that selected portions of the cornea are ablated by the pulses in accordance with the treatment algorithm;
   during treatment, directing to a photo detector from the last optical element in the system samples of said pulses of laser light being delivered to the cornea of the patient;
   comparing an output signal from the photo detector to a reference value derived from the treatment sequence and at least one previously measured photo detector output signal value for a pulse directed to the photodetector from the last optical element in the system; and
   providing an indication of the performance of the laser system in response to said comparison.

2. The method of claim 1, wherein the directing of portions of the energy of the pulses being delivered to the cornea of the patient is performed by transmitting the pulses through a beam splitter that is the last optical element in an optical path leading to the cornea of the patient.

3. The system of claim 1, wherein laser light pulses for ablating the cornea and detected by the photo detector are 193 nm UV light pulses.

4. The method of claim 1, wherein the pulses of laser light are controlled so that selected portions of the cornea are ablated by controlling the spatial dimensions of broad beam laser light pulses.

5. The method of claim 4, wherein the broad beam pulses have a spot diameter of from ½ to 8 mm on the cornea of the patient.

6. The method of claim 1,
   wherein the pulses of laser light are produced by a laser triggered by a triggering signal from a treatment computer;
   wherein the pulses of a laser light are spatially modulated responsive to signals from the treatment computer; and
   wherein the treatment computer employs a treatment algorithm appropriate for the patient to determine the spatial modulation of the pulse.

7. The method of claim 6, wherein a second, monitoring computer separately runs the treatment algorithm and provides the reference value responsive to separately inputted treatment parameters and the at least one previously measured photo detector output signal value.

8. The method of claim 6, wherein the comparison is initiated by the monitoring computer responsive to the laser triggering signal.

9. The method of claim 6, wherein the indication of performance is an alarm signal produced when the output signals from the photo detector for a predetermined number of pulses deviate a predetermined amount from the corresponding reference values.

10. The method of claim 6, further comprising the step of shutting down the laser system in response to an indication of performance failure.

11. A system for producing a predetermined treatment pattern of laser pulses for selectively ablating the cornea of a patient and for detecting a pattern of pulses as the pulses are being delivered to the patient comprising:
- a laser for producing laser light pulses;
- means for controlling pulses of laser light from the laser so that selected portions of the cornea of the patient are ablated in accordance with the predetermined treatment pattern including a first, treatment computer which runs a treatment algorithm based on inputted treatment parameters to produce the predetermined treatment pattern;
- a detector for producing signals during treatment indicative of the laser pulses being delivered to the patient over a selected time interval;
- a beam splitter for splitting the pulsed laser beam and directing to the detector samples of the pulses as they are delivered to the cornea; and
- a second, fail-safe computer for separately running the treatment algorithm to provide reference values for sampled pulses responsive to separately inputted treatment parameters, for comparing signals from the detector with the reference values and for providing an indication of performance of the system in response to the comparison.

12. The system of claim 11, further comprising means for producing a display of the spatial energy distribution of the laser pulses being delivered to the patient.

13. The system of claim 11 further comprising memory for storing energy distribution information derived from the signals produced by the detector.

14. The system of claim 11, wherein the system is a broad beam system using pulses having a spot diameter of from ½ to 8 mm on the cornea of the patient.

15. The system of claim 11, wherein the photo detector is an electronic camera and wherein the laser pulses are focused to produce images of the laser pulse spots.

16. The system of claim 11, further comprising means for controlling the system in response to the signals produced by the detector.

17. The system of claim 16, wherein the control of the system includes shutting down the system upon detection of an improper spatial energy distribution.

18. The system of claim 11, wherein the controlling means scans the laser pulses across an area of the cornea to be ablated.

19. The system of claim 18, wherein the system is a slit scanning laser system.

20. The system of claim 18, wherein the system is a flying spot scanner.

21. The system of claim 20, wherein the system uses laser spots having a diameter between 1 and 2 mm and a pulse rate between 50 and 200 Hz.

22. A system for producing a predetermined treatment sequence of laser light pulses of varying dimension for ablating the cornea of a patient and for continuously monitoring the predetermined treatment sequence being delivered to the patient comprising:
- a laser for producing laser light pulses;
- a spatial modulator for varying the dimensions of spots projected on the cornea by the laser light pulses;
- treatment electronic means for controlling the laser and spatial modulator in accordance with entered data indicative of the predetermined treatment sequence for the patient;
- a beam splitter for reflecting a portion of the electromagnetic energy of the laser light pulses delivered to the cornea of the patient and transmitting a portion of the electromagnetic energy of the same laser light pulses, the beam splitter being the last optical element in an optical path leading from the laser to the cornea of the patient;
- a laser pulse detector optically coupled to the beam splitter and receiving said portion of electromagnetic energy transmitted through the beam splitter for producing monitoring signals indicative of the laser light pulses delivered to the patient; and
- means for comparing the monitoring signals with reference values for the predetermined sequence of laser light pulses.

23. The system of claim 22, wherein the treatment electronic means triggers the laser to produce a light pulse and triggers a comparison of the monitoring signal with a corresponding reference value.

24. The system of claim 22, wherein the laser is a pulsed excimer laser and the spatial modulator includes an iris and slit of varying size, whose size is electronically controlled by the treatment electronic means.

25. The system of claim 22, further comprising a beam homogenizer between said laser and said spatial modulator.

26. The system of claim 22, wherein the laser pulse detector is an electro-optic detector which converts a split portion of electromagnetic energy of the laser pulse from the beam splitter to fluorescent light which is then used to produce an electronic signal.

27. The system of claim 22, further comprising an optical baffle between the beam splitter and the detector for absorbing light scattered by foreign material on the beam splitter.

28. The system of claim 22, wherein the laser pulse detector is an electro-optic detector for producing electronic monitoring signals in response to 193 nm UV light pulses.

29. The system of claim 22, wherein said comparing means comprises:
- monitoring electronic means for producing reference values indicative of the expected energy of laser pulses to be delivered to the cornea of the patient, said reference values being calculated in accordance with the data indicative of the predetermined treatment sequence of pulses for the patient; and
- electronic means for comparing the monitoring signals with the corresponding reference values calculated by the monitoring electronic means.

30. The system of claim 29, wherein the treatment and monitoring electronic means are separately programmed digital computing devices.

31. The system of claim 30, wherein at least one of said computing devices stores a record of the pulses delivered during the treatment.

32. A system for producing a predetermined treatment sequence of laser pulses for selectively ablating the cornea of a patient and for monitoring the predetermined treatment sequences of pulses as the pulses are being delivered to the patient comprising:
- a laser for producing laser light pulses;
- means for controlling the size and energy of laser light pulses delivered to the cornea of a patient so that selected portions of the cornea of the patient are ablated in accordance with the predetermined treatment sequence;
- a laser pulse detector for producing monitoring signals during treatment indicative of the energy of the laser pulses delivered to the patient; and
- a beam splitter optically coupled to the laser pulse detector onto which the controlled laser light pulses are directed prior to reaching the cornea of the patient, the beam splitter having a front surface mirror for reflecting a portion of the energy of the controlled laser light pulses to deliver said portion to the cornea of the patient and for transmitting to the laser pulse detector samples of the delivered pulses, wherein the front surface of the front surface mirror is the last optical surface in an optical path leading from the laser to the cornea of the patient.

33. The system of claim 32, wherein the laser pulse detector produces monitoring signals related in value to the total energy of each of the pulses of light delivered to the cornea of the patient.

34. The system of claim 32, wherein the laser pulse detector comprises an area photo sensor for producing monitoring signals indicative of the spatial energy distribution of pulses of light delivered to the cornea of the patient.

35. The system of claim 32, wherein the controlling means controls the size of broad beam laser spots projected on the cornea of the patient.

36. The system of claim 35, wherein the pulses have a spot diameter of from ½ to 8 mm on the cornea of the patient and a repetition rate of 10 to 50 Hz.

* * * * *